(12) United States Patent
Yamamoto

(10) Patent No.: US 6,432,882 B1
(45) Date of Patent: Aug. 13, 2002

(54) METHOD AND APPARATUS FOR ATOMIZING AN ORGANIC COMPOUND

(76) Inventor: Christopher W. Yamamoto, 818 Suncrest La., Caldwell, ID (US) 83605

( * ) Notice: Subject to any disclaimer, the term of this patent is extended or adjusted under 35 U.S.C. 154(b) by 114 days.

(21) Appl. No.: 09/668,827

(22) Filed: Sep. 22, 2000

(51) Int. Cl.$^7$ ............................................. A01N 47/20

(52) U.S. Cl. ................................. 504/304; 504/116.1

(58) Field of Search .............................. 504/304, 116.1

(56) References Cited

U.S. PATENT DOCUMENTS

| | | | |
|---|---|---|---|
| 4,226,179 A | | 10/1980 | Sheldon et al. |
| 4,887,525 A | | 12/1989 | Morgan |
| 5,129,951 A | * | 7/1992 | Vaughn et al. ................. 71/122 |
| 5,139,562 A | * | 8/1992 | Vaughn et al. ................. 71/88 |
| 5,436,226 A | * | 7/1995 | Lulai et al. ................. 504/291 |
| 5,723,184 A | | 3/1998 | Yamamoto |
| 5,935,660 A | | 8/1999 | Forsythe et al. |

* cited by examiner

Primary Examiner—S. Mark Clardy
(74) Attorney, Agent, or Firm—Angus C. Fox, III

(57) ABSTRACT

Several methods and multiple apparatus are disclosed for atomizing or vaporizing chlorpropham or any other organic compound that is a solid at ambient temperature and pressure conditions, without the need for converting the compound to a liquid which must be contained and transported by the aerosol-generating apparatus. The method provides an air stream that can be nearly saturated with chlorpropham vapor and free of both combustion products and carrier solvents. The process includes the steps of forming minute particles of solid CIPC particles from a larger block or chunks of solid CIPC, and inducting the particles into an airstream wherein the particles are provided with sufficient thermal energy to convert them into an aerosol. The process may be implemented by abrading a block of solid CIPC with a wire brush, by shaving a block of solid CIPC with a blade, or by pulverizing chunks of solid CIPC to convert it to a powder. Pulverization may be accomplished, for example, by placing the chunks in a chamber having a spinning blade. Alternatively, pulverization may be accomplished by passing the abraded or shaved CIPC particles through rapidly spinning turbine blades. The pulverized CIPC particles are routed to a heated chamber which, preferably, contains a series of baffles which repeatedly deflect and heat the airstream. The pulverized CIPC particles are converted to an aerosol or vapor within the heated chamber. The process has been used to convert solid CIPC to an aerosol at the rate of more than 20 kg per hour. Once conversion to an aerosol is complete, the airstream is directed to a potato storage facility and allowed to bathe tubers stored therein.

29 Claims, 5 Drawing Sheets

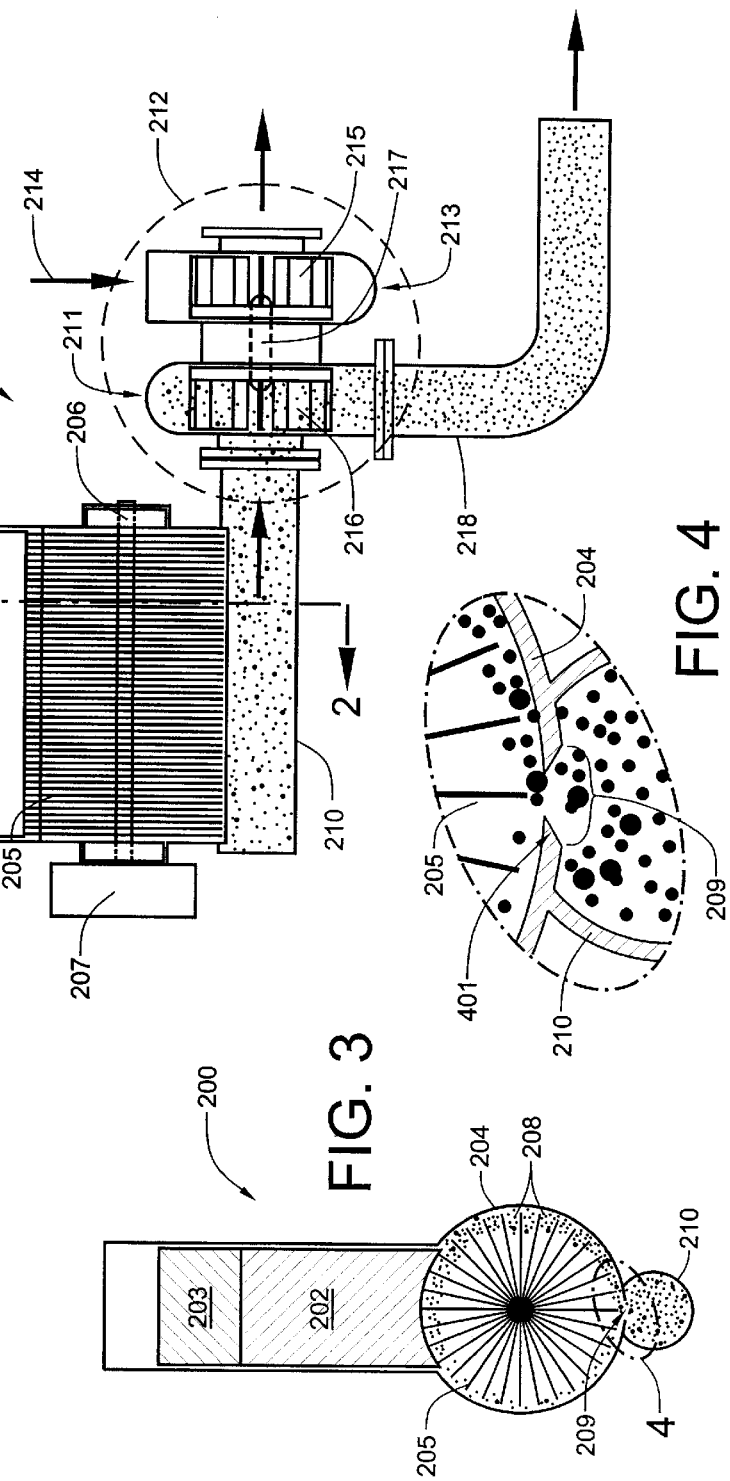
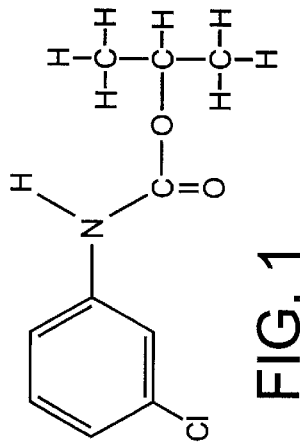

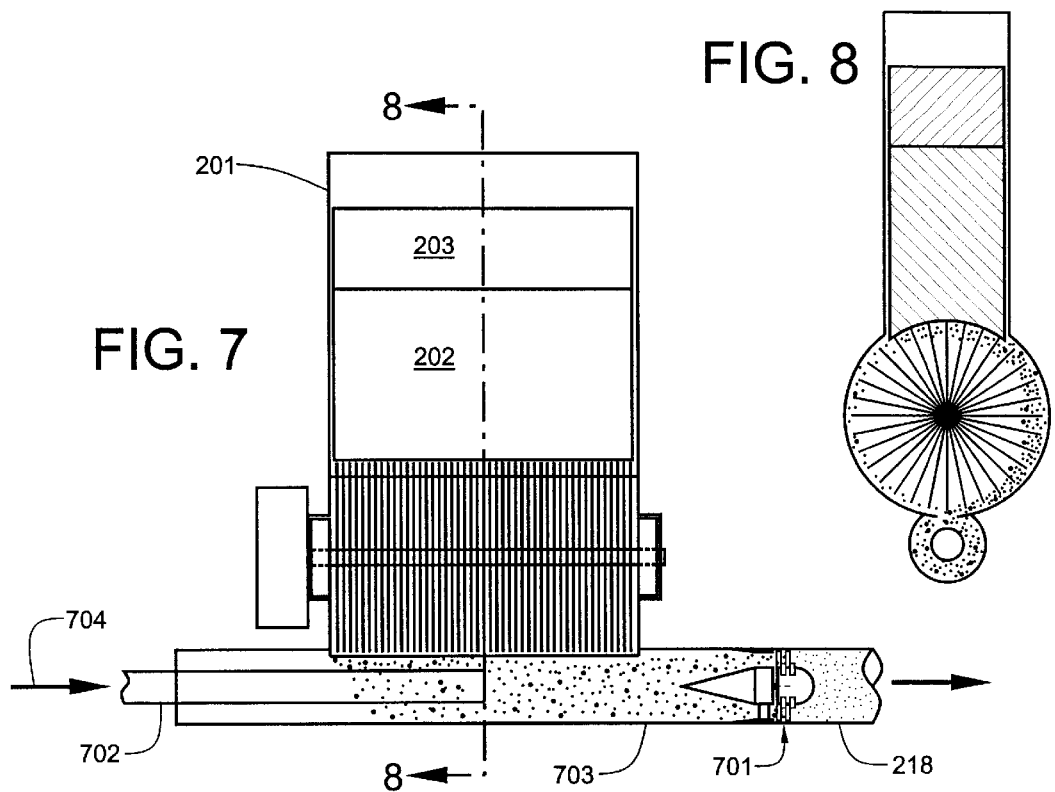
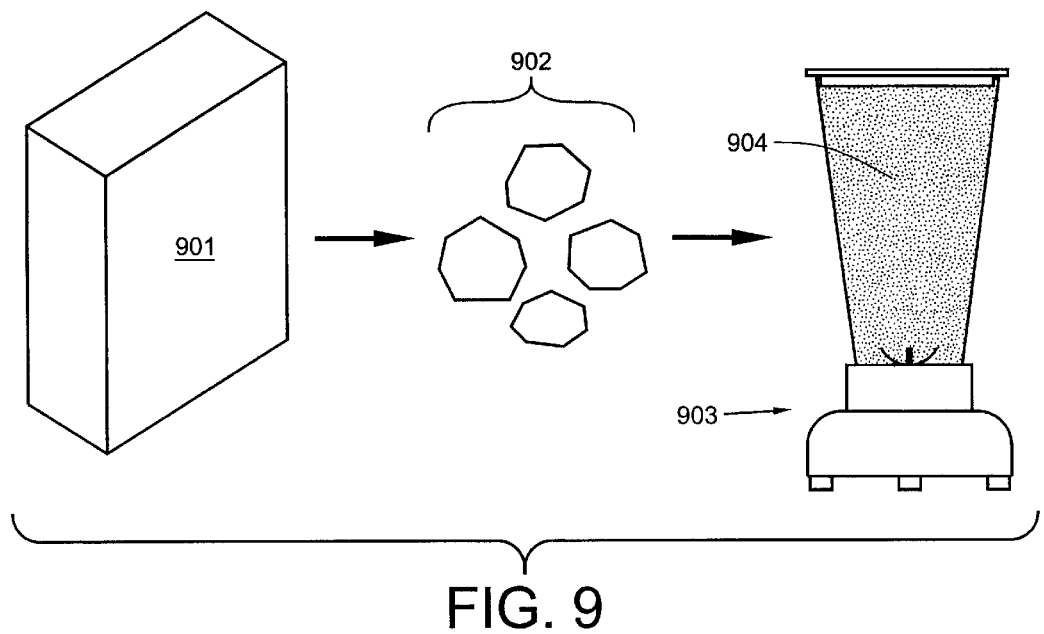

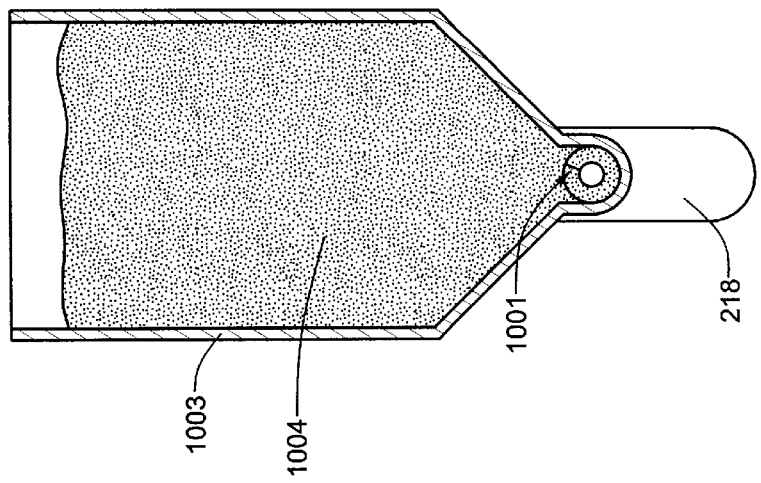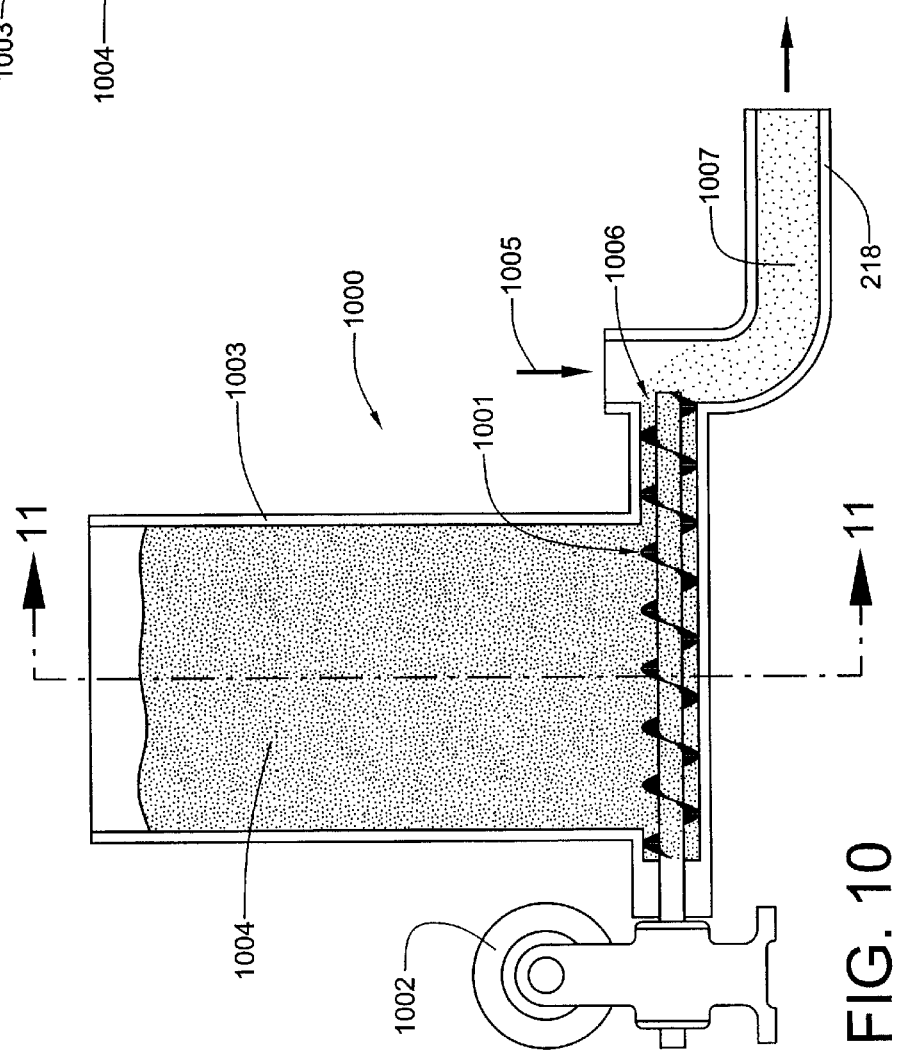

METHOD AND APPARATUS FOR ATOMIZING AN ORGANIC COMPOUND

BACKGROUND OF THE INVENTION

1. Field of the Invention

This invention relates to a method and apparatus for making organic compound particles and, subsequently, atomizing those particles. The invention is disclosed in the context of a method and apparatus for atomizing chlorpropham, a compound widely used in the agricultural industry to inhibit sprouting of stored tubers.

2. Description of Related Art

It is often desirable to store certain agricultural produce until a sale under favorable economic terms can be consummated and the produce delivered to the purchaser. During storage, it is essential that freshness of the produce be maintained. Tubers, such as potatoes, are frequently stored as bulk piles in quantities of 2,270,000 to over 22,700,000 kilograms (5,000,000 to over 50,000,000 U.S. lbs.) in dark, underground storage cellars where the temperature is maintained within a range of about 4.5° C. to 12.8° C. (approximately 40 to 55° F.). Untreated tubers will generally sprout over time, even in the absence of light. If the sprouting is allowed to continue unchecked, the tubers become commercially worthless. Isopropyl-3-chlorocarbonilate, an organic compound commonly known as CIPC or chlorpropham and marketed under a variety of trade names, is currently the only registered post-harvest sprout inhibitor used in potato storages in the United States. Used also as an herbicide, Its use as a potato sprout inhibitor was first reported by P. C. Marth in 1952, and its use for that purpose was later patented by the Pittsburgh Plate & Glass Co. The molecular structure of CIPC is depicted in FIG. 1. CIPC has a molecular weight of 213.66, a melting point of about 41° C., a vaporization temperature of about 246° C., and a vapor flash point of about 427° C.

CIPC inhibits potato sprout development by interfering with spindle formation during cell division. Cell division is extremely important during the wound healing or curing period after potatoes are placed into storage. Wound healing requires the production of two to five new cell layers formed by cell division. If CIPC is applied to the potatoes before the wound healing process is complete, excessive losses due to tuber dehydration and disease can occur. CIPC may be applied any time after the wound healing process is complete but before the tubers break dormancy in early spring. It is not recommended to store In order to suppress the sprouting of a tuber, the tuber must be covered with a thin film of chloroprofam. CIPC is applied to the tubers as an aerosol or as an emulsifiable concentrate. The emulsifiable concentrate is generally applied to the potatoes as a direct spray during the fresh packing operation. CIPC aerosols are generally applied to potatoes in bulk storage.

Several methods have been developed for applying CIPC aerosols to potatoes in bulk storage. U.S. Pat. No. 4,226,179 to Sheldon, III et al. discloses a process whereby CIPC, either without solvent or with a relatively small amount of solvent, is atomized at a temperature of less than 121° C. The aerosol is formed in a fogger having a cylindrical mist chamber in which ultrasonic resonance nozzles atomize the chemical agent. A tangentially introduced air flow and a helical baffle plate in the mist chamber cause centrifugal separation, leaving smaller particles near the center of the mist chamber. These small particles are carried by an airflow duct to a storage chamber containing potatoes. The aerosol condenses on the potatoes, thereby forming a growth is inhibiting film thereon. U.S. Pat. No. 5,723,184 to Yamamoto discloses a process whereby CIPC is heated to a molten state, pressurized, further heated and introduced into a heated airstream that is ducted to a storage chamber containing potatoes. U.S. Pat. No. 5,935,660 to Forsythe, et al. discloses a process similar to that of Yamamoto whereby solid CIPC is melted and then converted to an aerosol either by a pressurized hot air stream or by a combustion gas stream.

There are several drawbacks to the aerosol formation processes which inject molten CIPC into a heated airstream. The first is that of CIPC solidifying within the transport or injector lines. If an aerosol generation system having molten CIPC within the transport or injector lines is allowed to cool, the CIPC will solidify, making further operation of the equipment impossible until the CIPC returns to its molten state. In order to effectively deal with this operational quirk, molten CIPC must be removed from the transport lines when the equipment is shut down. This is typically done by replacing the molten CIPC with a solvent. Nozzle clogging can also be a problem with this type of equipment. If movement of the heated liquid CIPC is relied on to maintain the temperature of fluid transport lines removed from a primary heat source, nozzle clogging will result in solidification of CIPC within the transport lines within a short time. For this reason, liquid transport lines must also be heated. A second drawback related to the use of melted CIPC is the risk of scalding and burns to equipment operators, whether it be from the leakage of the scaldingly hot liquid CIPC from the liquid transport lines, or the need to repair application equipment containing melted CIPC. Though the maintenance risk may be minimized by allowing the equipment is to cool to safer, lower temperatures, the CIPC in the liquid transport lines will solidify at those safer temperatures, thereby hampering efforts to restart the aerosol generation process. A third drawback to the use of melted CIPC for the generation of aerosols is that of equipment warm up time. The equipment and the solid CIPC act as a heat sink, which must be raised to operational temperatures for the aerosol generation process to function properly.

What is needed is a new CIPC aerosol generation process which does not require the conversion of solid CIPC to a liquid which must be contained by the aerosol generating equipment prior to its conversion to an aerosol.

SUMMARY OF THE INVENTION

The present invention provides both a method and multiple apparatus for atomizing chlorpropham (CIPC) or any other similar organic compound which does not require the conversion of solid CIPC to a liquid which must be contained and transported by the aerosol generating equipment prior to its conversion to an aerosol. The process includes the steps of forming minute particles of solid CIPC particles from a larger block or chunks of solid CIPC, and inducting the particles into an airstream wherein the particles are provided with sufficient thermal energy to convert them into an aerosol. The process may be implemented by abrading a block of solid CIPC with a wire brush, by shaving a block of solid CIPC with a blade, or by pulverizing chunks of solid CIPC to convert it to a powder. Pulverization may be accomplished, for example, by placing the chunks in a chamber having a spinning blade. A common food blender on a high-speed setting will produce CIPC powder having a consistency similar to that of talcum powder. For a first embodiment of the invention, the block of solid CIPC is slidably inserted within a chute that connects with a cylindrically shaped housing. The brush, also cylindrically shaped, revolves about its axis, which coincides with that of the housing. Particles abraded by the brush are drawn by differential air pressure through a slot at the base of the housing into an intake manifold having a moving air stream. The air stream is motivated by the propeller of a turbine, to which the manifold is coupled. The impeller inlet of the turbine is coupled to a source of compressed air. The turbine propeller, which is spun at speeds comparable to those achieved by an automotive turbocharger, also pulverizes the abraded particles. From the turbine propeller outlet, the air stream is routed to a heated chamber which, preferably, contains a series of baffles which repeatedly deflect and heat the airstream. The pulverized CIPC particles are converted to an aerosol within the heated chamber. The process has been used to convert solid CIPC to an aerosol at the rate of more than 20 kg per hour. Once conversion to an aerosol is complete, the airstream is directed to a potato storage facility and allowed to bathe tubers stored therein. In the case where CIPC particles are shaved from a solid block, the particles may be passed through rapidly spinning blades, which pulverize the particles into CIPC dust. The blades are preferably spun with an air-powered motor or, alternatively, with an electric motor. In the case where the CIPC is pulverized to dust and subsequently loaded in a hopper from which it is fed to a heated air stream, the particles are sufficiently small as to require no further treatment prior to heating. One consideration is that a mass of pulverized CIPC particles tend to agglomerate with time. Therefore, it may be desirable to stir the particles continually, or at least periodically, in order to slow the agglomeration process. Agglomeration may also be slowed by cooling the pulverized mass of CIPC particles. However, cooled particles require more heat input to convert them to an aerosol. The pulverized CIPC particles may be fed from the hopper into the airstream via a wire-brush auger. Continual vibration to the mass of pulverized particles to prevent bridging of the particles within the hopper that would interfere with the entry of particles into the auger intake port.

BRIEF DESCRIPTION OF THE DRAWINGS

FIG. 1 depicts the chemical structure of chlorpropham;

FIG. 2 is a schematic front elevational view of a first embodiment apparatus for abrading a block of solid CIPC and converting the abraded particles to an aerosol;

FIG. 3 is a cross-sectional view of the first embodiment apparatus, taken through plane 3—3 of FIG. 2:

FIG. 4 is a close-up view of region 4 of FIG. 3;

FIG. 7 is a schematic front elevational view of a derivative of the first embodiment apparatus;

FIG. 8 is a cross-sectional view of the apparatus of FIG. 7, taken through plane 8—8 of FIG. 7;

FIG. 9 visually depicts a process for converting a block of solid CIPC to powder;

FIG. 10 is schematic front elevational view of a third embodiment apparatus for converting CIPC in powder form to an aerosol;

FIG. 11 is a cross-sectional view of the apparatus of FIG. 10, taken through plane 11—11 of FIG. 10.

PREFERRED EMBODIMENT OF THE INVENTION

The present invention provides both a method and multiple apparatus for atomizing chlorpropham (CIPC) or any other similar organic compound. The method does not require the conversion of solid CIPC to a liquid, containment and transport of that liquid, and subsequent conversion of that liquid to an aerosol. The process includes the steps of forming minute particles of solid CIPC particles from a block or chunks of solid CIPC, and inducting the particles into an airstream wherein the particles are provided with sufficient thermal energy to convert them into an aerosol. The process may be implemented by abrading a block of solid CIPC with a wire brush, by shaving a block of solid CIPC with a blade, or by pulverizing chunks of solid CIPC to convert it to a powder.

For the purposes of this disclosure, atomization produces an "aerosol" that may be described as a colloidal suspension within an air mass of single large molecules or droplets consisting of multiple smaller molecules. Vaporization, on the other hand, implies that all liquid molecules have been converted to the gas phase. In the gas phase, the individual molecules have sufficient kinetic energy to overcome the attractive forces which would normally cause the molecules to condense to the liquid state. Whether the gas phase or the aerosol phase prevails is largely a question of energy input. An aerosol is easily converted to the gas phase state through the input of energy. The method provides an air stream that can be nearly saturated with atomized chloroprofam and free of both combustion products and carrier solvents. In addition, the temperature of the air stream can be maintained at a temperature that is sufficiently low that it will not adversely affect tubers which are bathed in the aerosol. The apparatus required to practice the method is far less complex than equipment currently employed to produce atomized CIPC having similar characteristics.

Figure 5:
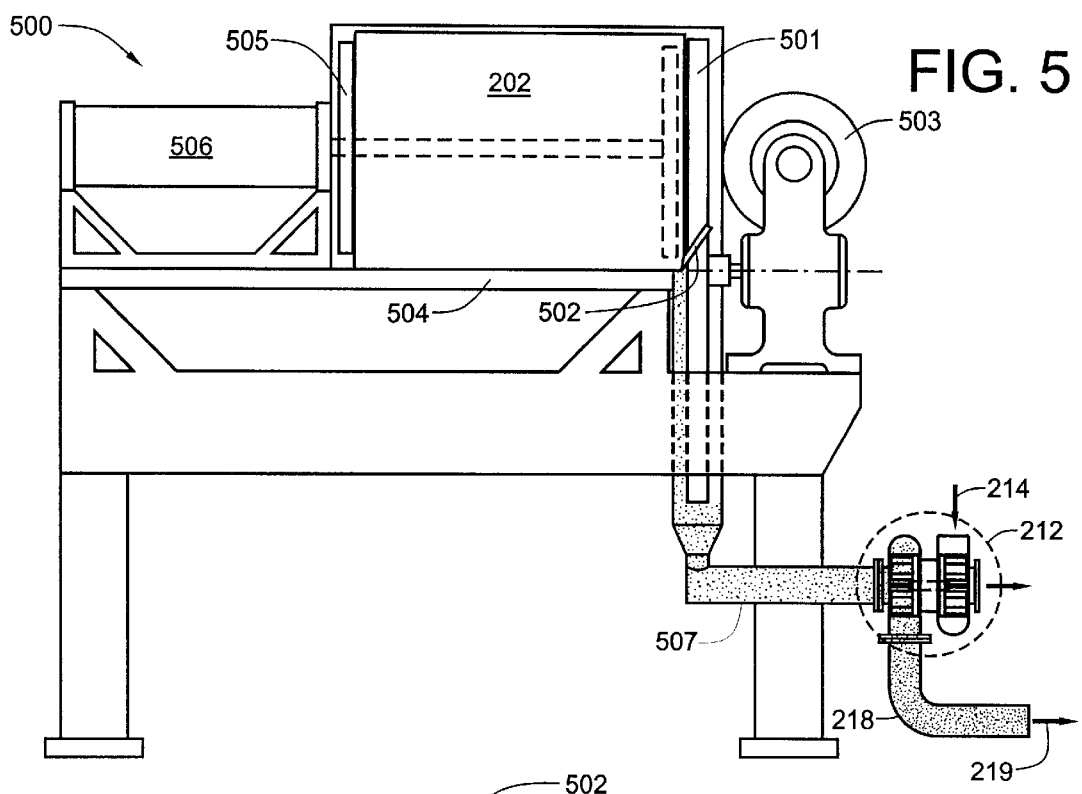
FIG. 5 is a schematic front elevational view of a second embodiment apparatus for shaving a block of solid CIPC and converting the shaved particles to an aerosol.
Figure 6:
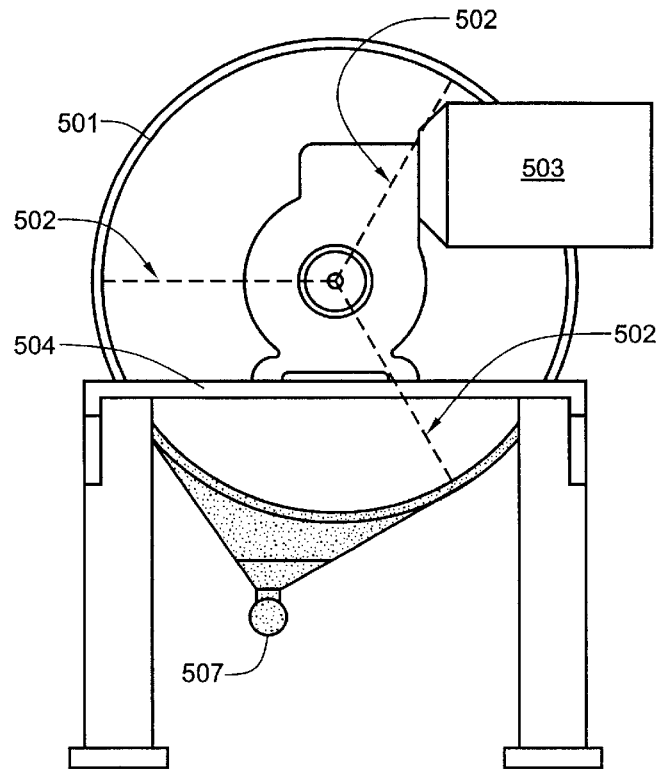
FIG. 6 is a schematic right end elevational view of the apparatus of FIG. 5 with the turbine assembly removed.
Figure 12:
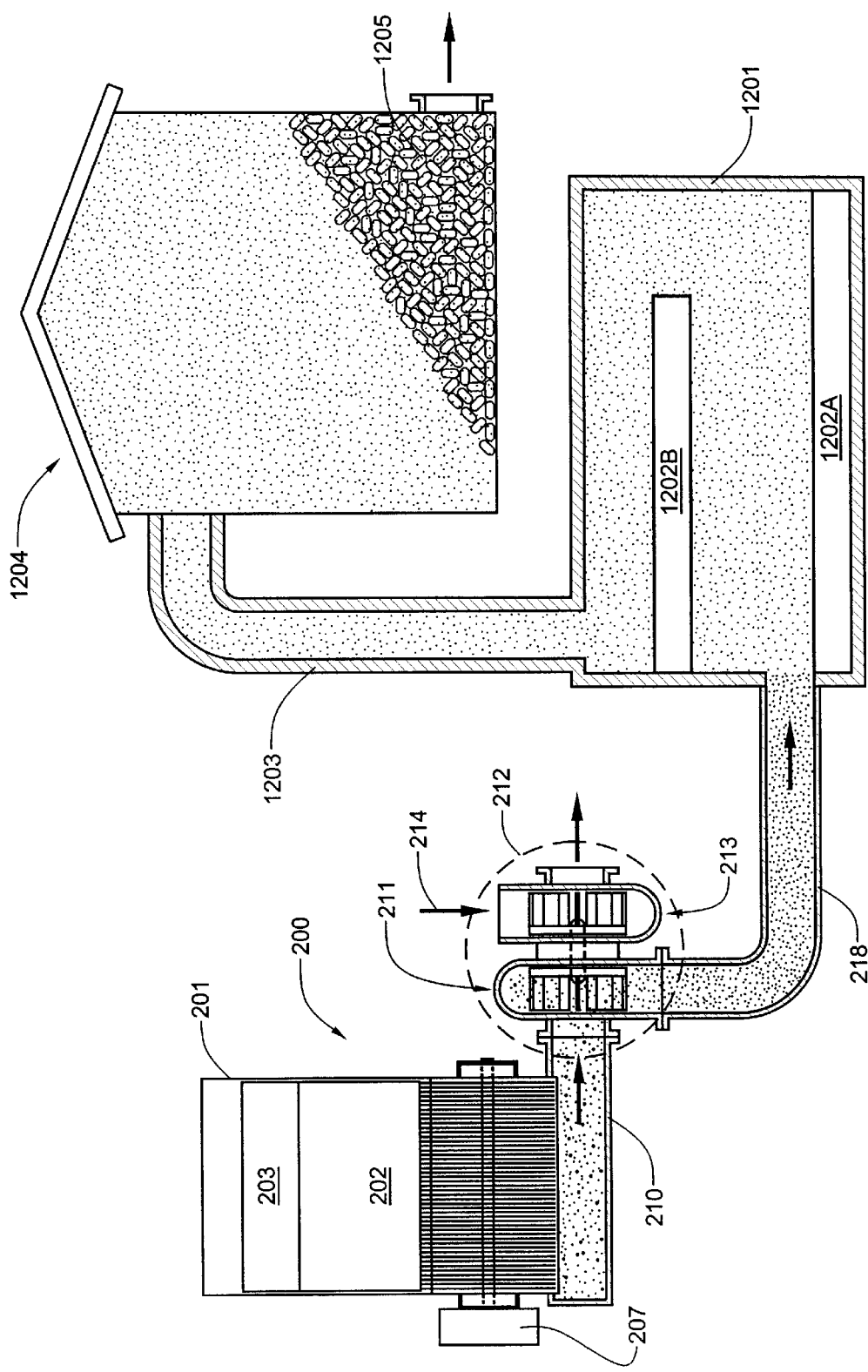
FIG. 12 is an elevational view of the first embodiment apparatus in combination with a heater box and a tuber storage facility.

Referring now to FIGS. 2 and 3, a first embodiment particle generation apparatus 200 includes a vertically-oriented chute 201 of rectangular cross section for receiving a block of solid CIPC 202. Solid CIPC is typically supplied in 10 lb. (about 4.545 kg.) blocks having dimensions of about 15 in.×7 in.×3 in. (roughly 38 cm.×7.6 cm.×17.8 cm.). The chute is sized to accept the blocks lengthwise, being approximately 7.5 in.×3.5 in. (roughly 19 cm.×8.9 cm.) For loading convenience, the chute 201 may be of sufficient length to accept multiple blocks 202 simultaneously, with room for a 6 to 10 lb. weight 203 to be placed thereupon. The chute intersects a cylindrical chamber 204 which houses an axially mounted, cylindrically-shaped, rotatable wire brush 205. The wire brush has an axial shaft 206 that is supported at opposite ends of the cylindrical chamber 204. A motor 207 rotates the wire brush 205, which contacts a horizontally-disposed side of the CIPC block 202. The weighted block 203 is placed on top of the CIPC block 202 in order to increase the force with which the CIPC block 202 contacts the wire brush 205. The CIPC block 202 is abraded at a relatively constant rate by the rotating wire brush 205. Using presently preferred operational parameters, the wire brush 205 is rotated at an angular velocity of about 250 rpm. Abraded particles 208 from the CIPC block fall or are swept by the rotating wire brush 204 to the bottom of the cylindrical chamber 203, where they are drawn through an particle exit slot 209 at the bottom of the cylindrical chamber 203 by a pressure gradient into a turbine intake manifold 210. The intake manifold 210 is coupled to the propeller section 211 of an pressurized-gas-powered turbine 212. An impeller section 213 is coupled to a source of high-pressure gas 214 (e.g., compressed air from a compressor). The impeller 214 is coupled to the propeller 216 via a drive shaft 217. Propeller/impeller rotational speeds greater than 20,000 r.p.m. may be easily attained. The propeller section 211 generates a lower-than-atmospheric pressure condition in the intake manifold 210 and a higher-than-atmospheric pressure condition in the transport tube 218 downstream from the propeller section 211 that is responsible for the flow of an air stream 219 through the chute 201, through the cylindrical chamber 203, into the intake manifold 210, through the turbine 212, and into the transport tube 218. As will be subsequently shown, the particles and conveying air stream are carried by the transport tube 218 to a heating chamber (see item 1201 of FIG. 12) where the particles are converted to an aerosol/vapor. The aerosol/vapor is then ducted to a tuber storage facility (see item 1204 of FIG. 12), where the aerosol/vapor condenses on the tubers in an amount sufficient to prevent sprouting.

Referring now to FIG. 4, the shape of the slot 209 is shown in greater detail. The slot 209, which extends the length of the cylindrical chamber 204, has chamfered edges 401 which also extend the length of the cylindrical chamber 204 and which face the interior of the intake manifold 210. It is believed that the chamfered edges 401 of slot 209 contribute to the smooth flow of CIPC particles 208 into the intake manifold 210.

Referring now to FIGS. 5 and 6, a second embodiment particle generation apparatus 500 is adapted from an apparatus designed to produce and blast sublimable granules on demand. The apparatus is described in detail in a 1996 U.S. patent (U.S. Pat. No. 5,520,572) issued issued to Alan E. Opel, et al. The apparatus, though designed to produce solid carbon dioxide granules, may also be employed to produce solid CIPC granules. The apparatus functions very much like an ice shaving machine used by snow-cone vendors. The second embodiment apparatus 500 incorporates a wheel 501 in which three angled blades 502 are fixed. The wheel 501 is rotated by a motor 503 powered by either electricity or pressurized air. A block of the material to be shaved (in this case the CIPC block 202 is installed on a platform 504 between the wheel 501 and a ram 505 actuated by a fluid or gas pressurized cylinder 506. For the present application, the block 202 is preferably fed at a constant rate toward the wheel 501. As the block moves toward the rotating wheel 501, the blades 502 shave off CIPC particles from the block's leading edge. When a block 202 has been completely consumed, the ram is retracted and a new block is placed between the ram 505 and the wheel 501. As for the first embodiment depicted in FIGS. 2 through 4, a gas-powered turbine 212 is placed in the particle transport path 507 in order to pulverized the shaved particles to a dust-like consistency.

Referring now to FIGS. 7 and 8, a third embodiment apparatus 700 for generating CIPC particles is shown. This apparatus is a variant of the first embodiment apparatus heretofore described with reference to FIGS. 2 through 4. The primary differences which characterize the third embodiment apparatus 700 are a reliance on a pressurized air stream to transport the abraded CIPC particles 208 to the heating chamber. Rapidly rotating blades 701, which may be driven by either an electric motor or an air motor, pulverize the abraded particles 208, but contributes little to the airflow used to transport the particles 208. A pressurized air supply line 702 is installed concentrically within a particle receiving chamber 703, which roughly corresponds to the turbine intake manifold 210 of the first embodiment apparatus 200. The supply line 702 extends to approximately the middle of the particle exit slot 209. As the high-pressure air 704 rushes below the slot 209, a low pressure region is created within the particle receiving chamber, thereby creating a flow of air through the chute 201, through the cylindrical chamber 203, into the particle receiving chamber 703, through the blades 701, and into the transport tube 218. The transport tube 218 conveys the particles and air to a heated chamber (see item 1201 of FIG. 12), where the particles are converted to an aerosol or vapor. The aerosol or vapor is then conveyed to a tuber storage facility for treatment of stored tubers (see item 1204 of FIG. 12).

Referring now to FIG. 9, a process is described whereby a solid block of CIPC 901 is converted to chunks of solid CIPC 902, and those chunks are subsequently converted to a powder. It has been determined that when chunks of CIPC are subjected to the rotating blades of a conventional food blender 903 operating at a high-speed setting, the CIPC is converted to a powder 904 having a consistency similar to that of talcum power. This power can then be fed into an air stream within transport tube 218 at a controlled rate, and converted directly into an aerosol/vapor by passing the airstream through a heated chamber (see item 1201 of FIG. 12). From the chamber, it is ducted to a tuber storage facility (see item 1204 of FIG. 12).

Referring now to FIGS. 10 and 11, a feed apparatus 1000 is shown which may be used to introduce powdered CIPC into a moving airstream at a controlled rate. A wire brush auger 1001 is rotated at a constant rate by a motor 1002 which may be powered by one of any known technologies (e.g., electricity or compressed air). The auger is fed by a hopper 1003 that is filled with powdered CIPC 1004. A compressed air source 1005 creates a moving air stream within a transport tube 218. Powdered CIPC 1004 is fed by the auger 1001 to an exit port 1006 coupled to the moving airstream 1007. The power-containing air stream 1007 is ducted by transport tube 218 to a heated chamber (see item 1201 of FIG. 12) and then to a tuber storage facility (see item 1204 of FIG. 12).

One of the problems related to the use of powdered CIPC is the compounds propensity to sublimate (i.e., pass from a solid phase to a gas phase at temperatures below its melting point). Therefore, if powdered CIPC is allowed to remain in a hopper for extended periods, the particles will agglomerate. Therefore, any powdered CIPC must be converted to an aerosol almost as soon as it is made. It should be apparent that a food blender may be easily replaced by suitable commercial equipment.

FIG. 12 shows an entire aerosol generation system fabricated in accordance with the present invention, and which employs the first embodiment particle generation apparatus 200. The transport tube 217 is coupled to a heated chamber 1201. The heated chamber 1201 incorporates at least one heated plate. This particular chamber incorporates a pair of heated plates 1202A and 1202B. The plates may be either electrically heated or heated by combustion. The plates are heated to temperatures within a range of about 415–460° C.(roughly 780–875° F.). It is desirable to heat the air stream and CIPC particles passing through the heated chamber 1201 to a temperature considerably above the CIPC vaporization temperature, yet safely below the CIPC vapor flash point. A safe, effective temperature is deemed to be within the range of about 350–400° C.(roughly 660–750° F.). If a longer path is employed through the heated chamber 1201, temperatures may be reduced to a level nearer the CIPC vaporization temperature (246° C.) without resultant condensation of the aerosol/vapor prior to reaching the tuber storage facility. Higher vapor temperatures have an advantage in that the duct 1203, which couples the heated chamber 1201 to the tuber storage facility 1204 containing tubers 1205, will not require active heating to prevent condensation, though it will likely require effective insulation.

For the process disclosed herein, it should be apparent that the smaller the CIPC particles, the more easily it is to convert them directly to an aerosol or vapor without buildup of liquid CIPC in the heating chamber 1201. When CIPC is pulverized to the consistency of talcum powder, in which average particles size is less than 0.025 mm, direct conversion of the particles to an aerosol or vapor proceeds with little or no buildup of liquid CIPC in the heating chamber 1201. It has been observed that when particle size increases about 0.1 mm, direct conversion becomes considerably more difficult, and CIPC losses through liquid residue increase significantly. Particle size, as it applies to particles of random shape, is defined in this disclosure as the longest dimension through any cross section of a particle.

It should be readily apparent from the above descriptions, that an improved method is provided for atomizing CIPC, without the need for, first, converting the substance to a liquid which must be contained, and which can be implemented by the embodiments of the heretofore described apparatus. It should also be apparent that any of the methods for creating fine particles may be used in combination with the heating chamber 1201 so that those particles may be converted to an aerosol or vapor.

Although only several embodiments of the method for atomizing solid chlorpropham and several embodiments of apparatus which may be utilized to implement the atomization methods are disclosed herein, it will be obvious to those having ordinary skill in the art that changes and modifications may be made thereto without departing from the scope and the spirit of the invention as hereinafter claimed.

What is claimed is:

1. A method for introducing an organic sprout-inhibiting compound that is a solid at ambient temperatures into an airstream, the method comprising the steps of:
   providing a ducted airstream;
   pulverizing an amount of the solid compound;
   introducing the pulverized solid compound into the ducted airstream at a controlled rate.

2. The method of claim 1, wherein the sprout-inhibiting compound is chlorpropham.

3. The method of claim 1, wherein pulverization is accomplished by abrading a block of solid sprout-inhibiting compound.

4. The method of claim 3, wherein the step of abrading is accomplished with a spinning wire brush held in contact with the block.

5. The method of claim 1, wherein pulverization is accomplished by the high-speed impact of chunks of the solid sprout-inhibiting compound with a generally non-deformable solid object.

6. The method of claim 5, wherein the high-speed impact with a non-deformable solid object is provided by rapidly spinning blades.

7. The method of claim 1, wherein pulverization is accomplished by shaving particles from a block of solid sprout-inhibiting compound with at least one cutting edge rotatable within a plane against a surface of said block.

8. The method of claim 7, which further comprises the step of passing the shaved particles through spinning turbine blades.

9. The method of claim 1, wherein the pulverized particles have cross-sectional dimensions of generally less than 0.1 mm.

10. The method of claim 1, wherein pulverization is accomplished exclusively by subjecting chunks of the sprout-inhibiting compound to at least one spinning blade in a chamber, thereby generating a quantity of powdered sprout-inhibiting compound that is loaded into a hopper and introduced into the airstream at a controlled rate.

11. The method of claim 1, wherein the solid particles are converted to an aerosol by heating the ducted airstream to a temperature that is above the melting point, but below the flash point of the sprout-inhibiting compound.

12. A method for applying a coating of an organic sprout-inhibiting compound, that is a solid at ambient temperatures, to tubers in a storage enclosure, the method comprising the steps of:
   (a) providing an airstream that is heated to a temperature that is above the melting point, but below the flash point of the compound;
   (b) pulverizing the solid sprout-inhibiting compound to generate a powder;
   (c) introducing the powder into the airstream; and
   (d) ducting the airstream to the storage enclosure so that the tubers are bathed with the sprout-inhibiting compound.

13. The method of claim 12, wherein the particles of pulverized compound have cross-sectional dimensions of generally less than 0.1 mm.

14. The method of claim 12, wherein the sprout-inhibiting compound is converted to an aerosol by the heated airstream.

15. The method of claim 12, wherein the sprout-inhibiting compound is converted to a vapor by the heated airstream.

16. The method of claim 12, wherein the sprout-inhibiting compound is converted to both an aerosol and a vapor by the heated airstream.

17. The method of claim 16, wherein abrading of the block of solid compound is accomplished bringing the block into contact with a spinning wire brush.

18. The method of claim 16, wherein particle generation through abrasion is maintained at a rate that is optimum for the immediate introduction of those particles into the airstream, there being no intermediate storage of particles prior to their introduction into the airstream.

19. The method of claim 12, wherein pulverization of the sprout-inhibiting compound is accomplished by abrading a block of the solid compound to form coarse particles and subsequently passing the particles through spinning turbine blades to pulverize the coarse particles.

20. The method of claim 12, wherein pulverization of the sprout-inhibiting compound is accomplished by shaving a block of the solid compound to form coarse particles and subsequently passing the particles through spinning turbine blades to pulverize the coarse particles.

21. The method of claim 20, wherein abrading of the block of solid compound is accomplished bringing the block into contact with a spinning wire brush.

22. The method of claim 20, wherein particle generation through abrasion is maintained at a rate that is optimum for the immediate introduction of those particles into the airstream, there being no intermediate storage of particles prior to their introduction into the airstream.

23. The method of claim 12, wherein said compound is chlorpropham, and the airstream is heated to a temperature within the range of about 350–400° C.

24. A method for converting solid chlorpropham into an aerosol, the method comprising the steps of:

(a) pulverizing the solid chlorpropham;

(b) introducing the pulverized chlorpropham into an airstream wherein the particles are provided with sufficient thermal energy to convert them into an aerosol.

25. The method of claim 24, wherein pulverization is accomplished by abrading a block of solid chlorpropham.

26. The method of claim 24, wherein pulverization is accomplished by shaving particles from a block of solid chlorpropham with at least one cutting edge.

27. The method of claim 24, wherein said airstream is heated to a temperature within the range of about 350–400° C.

28. The method of claim 24, wherein pulverization is accomplished by the high-speed impact of chunks of the solid chlorpropham with a generally non-deformable solid object.

29. The method of claim 28 wherein introduction of the pulverized chlorpropham into an airstream is accomplished by loading the powdered chlorpropham into a hopper having an attached metering device which introduces the powered chlorpropham into the airstream at a controlled rate.

* * * * *